(12) United States Patent
Cremer et al.

(10) Patent No.: US 10,820,935 B2
(45) Date of Patent: Nov. 3, 2020

(54) TENSIONING CABLE LOCKING DEVICE

(71) Applicant: Stryker European Holdings I, LLC, Kalamazoo, MI (US)

(72) Inventors: Axel Bernhard Cremer, Pleasantville, NY (US); Nicholas D. Morfing, Washingtonville, NY (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 0 days.

(21) Appl. No.: 15/887,525

(22) Filed: Feb. 2, 2018

(65) Prior Publication Data

US 2018/0221073 A1 Aug. 9, 2018

Related U.S. Application Data

(60) Provisional application No. 62/454,266, filed on Feb. 3, 2017.

(51) Int. Cl.
*A61B 17/88* (2006.01)
*A61B 17/82* (2006.01)
(Continued)

(52) U.S. Cl.
CPC .......... *A61B 17/8869* (2013.01); *A61B 17/82* (2013.01); *A61B 17/842* (2013.01); *A61B 17/7053* (2013.01); *A61B 2017/00933* (2013.01)

(58) Field of Classification Search
CPC ... A71B 17/8869; A61B 17/82; A61B 17/842; B62J 11/00
See application file for complete search history.

(56) References Cited

U.S. PATENT DOCUMENTS

| 1,159,863 A | 4/1913 | Park |
| 2,226,393 A | 12/1940 | Seeger et al. |

(Continued)

FOREIGN PATENT DOCUMENTS

| DE | 8203609 U1 | 6/1982 |
| DE | 9417019 U1 | 1/1995 |

(Continued)

OTHER PUBLICATIONS

Extended European Search Report for EP Application No. 18154877, dated Jun. 28, 2018.

(Continued)

*Primary Examiner* — Tessa M Matthews
(74) *Attorney, Agent, or Firm* — Lerner, David, Littenberg, Krumholz & Mentlik, LLP

(57) ABSTRACT

A tension device for applying tension to an orthopedic cable loop system is designed to remain implanted in vivo after completion of the surgical procedure in which the device is used. The tension device may include a spool rotatable in one direction, such as by having outer flanges engageable with ratcheting protrusions along a cavity within the body of the device. The tension device may maintain a biasing force on the cable, which force may be applied by an elastic material. For example, the elastic may be provided in an opening of the body of the device. In another example, the elastic may be provided in the spool, such as by constructing the flanges of the spool from elastic material or by providing elastic material between an inner and an outer ring of the spool. Other biasing components as well as measuring components may be provided in the tension device.

18 Claims, 6 Drawing Sheets

(51) Int. Cl.
*A61B 17/00* (2006.01)
*A61B 17/84* (2006.01)
*A61B 17/70* (2006.01)

(56) References Cited

U.S. PATENT DOCUMENTS

| | | | |
|---|---|---|---|
| 2,292,746 A | | 8/1942 | Donald |
| 3,080,867 A | | 3/1963 | Eichinger |
| 3,533,588 A | * | 10/1970 | Cregier .................. B60P 7/083 24/269 |
| 3,644,966 A | | 2/1972 | Higgins |
| 4,262,391 A | * | 4/1981 | Peash ..................... F16L 33/02 217/95 |
| 4,546,524 A | * | 10/1985 | Kreft ....................... F16L 33/02 24/19 |
| 4,889,110 A | | 12/1989 | Galline et al. |
| 4,966,600 A | | 10/1990 | Songer et al. |
| 5,070,805 A | | 12/1991 | Plante |
| 5,190,545 A | | 3/1993 | Corsi et al. |
| 5,356,412 A | * | 10/1994 | Golds ................ A61B 17/1327 24/170 |
| 5,383,905 A | | 1/1995 | Golds et al. |
| 5,395,374 A | | 3/1995 | Miller et al. |
| 5,415,658 A | | 5/1995 | Kilpela et al. |
| 5,423,820 A | | 6/1995 | Miller et al. |
| 5,569,253 A | | 10/1996 | Farris et al. |
| 5,607,429 A | | 3/1997 | Hayano et al. |
| 5,607,430 A | | 3/1997 | Bailey |
| 5,649,927 A | | 7/1997 | Kilpela et al. |
| 5,653,711 A | | 8/1997 | Hayano et al. |
| 5,665,089 A | | 9/1997 | Dall et al. |
| 5,702,399 A | | 12/1997 | Kilpela et al. |
| 5,720,747 A | | 2/1998 | Burke |
| 5,741,259 A | | 4/1998 | Chan |
| 5,788,697 A | | 8/1998 | Kilpela et al. |
| 5,810,824 A | | 9/1998 | Chan |
| 5,810,825 A | | 9/1998 | Huebner |
| 5,868,748 A | | 2/1999 | Burke |
| 5,888,221 A | | 3/1999 | Gelbard |
| 5,935,133 A | | 8/1999 | Wagner et al. |
| 5,964,769 A | | 10/1999 | Wagner et al. |
| 5,993,452 A | | 11/1999 | Vandewalle |
| 6,017,347 A | | 1/2000 | Huebner et al. |
| 6,051,007 A | * | 4/2000 | Hogendijk ............. A61B 17/08 606/151 |
| 6,053,921 A | | 4/2000 | Wagner et al. |
| 6,086,590 A | | 7/2000 | Margulies et al. |
| 6,338,734 B1 | | 1/2002 | Burke et al. |
| 6,391,030 B1 | | 5/2002 | Wagner et al. |
| 6,520,965 B2 | | 2/2003 | Chervitz et al. |
| 6,682,533 B1 | | 1/2004 | Dinsdale et al. |
| 6,960,213 B2 | | 11/2005 | Chervitz et al. |
| 8,142,434 B2 | | 3/2012 | Bluechel |
| 8,343,155 B2 | | 1/2013 | Fisher et al. |
| 8,764,809 B2 | | 7/2014 | Lorenz et al. |
| 9,101,426 B2 | | 8/2015 | Forderer et al. |
| 2002/0026694 A1 | * | 3/2002 | Bremicker ............... B62J 11/00 24/483 |
| 2003/0187434 A1 | | 10/2003 | Lin |
| 2004/0097942 A1 | | 5/2004 | Allen et al. |
| 2004/0172028 A1 | | 9/2004 | Roger |
| 2005/0171547 A1 | | 8/2005 | Aram |
| 2006/0058795 A1 | | 3/2006 | Boyd |
| 2006/0135958 A1 | | 6/2006 | Marissen et al. |
| 2006/0206114 A1 | | 9/2006 | Ensign et al. |
| 2006/0235401 A1 | | 10/2006 | Baldwin et al. |
| 2006/0276896 A1 | | 12/2006 | Fallin et al. |
| 2007/0233075 A1 | | 10/2007 | Dawson |
| 2009/0082820 A1 | | 3/2009 | Fielding et al. |
| 2010/0036424 A1 | | 2/2010 | Fielding et al. |
| 2016/0038199 A1 | | 2/2016 | Wiederkehr et al. |
| 2016/0228152 A1 | | 8/2016 | Robinson et al. |

FOREIGN PATENT DOCUMENTS

| | | |
|---|---|---|
| EP | 0019062 A1 | 11/1980 |
| EP | 0791338 A2 | 8/1997 |
| EP | 0955013 A1 | 11/1999 |
| FR | 2614781 A1 | 11/1988 |
| GB | 235167 A | 7/1926 |
| GB | 2311664 A | 10/1997 |
| GR | 1003502 B | 1/2001 |
| WO | 1993003681 A1 | 3/1993 |
| WO | 1993018716 A1 | 9/1993 |
| WO | 1994028812 A1 | 12/1994 |
| WO | 1995022294 A1 | 8/1995 |
| WO | 1998035623 A1 | 8/1998 |
| WO | 2002067769 A2 | 9/2002 |
| WO | 2004019797 A2 | 3/2004 |
| WO | 2004107996 A1 | 12/2004 |
| WO | 2007047467 A1 | 4/2007 |
| WO | 2008019511 A1 | 2/2008 |

OTHER PUBLICATIONS

AcroMed Publication, "AcroMed Spinal Solutions for Cervical Pathologies," Jul. 1995, pp. 1-8.
Cable Ready Cable Grip System, "Comprehensive Cable Grip System: Family Ties", 97-223201 20ML, 2001 Zimmer, Inc., US.
Dall-Miles Recon and Trauma Cable System Surgical Protocol, Literature No. LSP63, MS/GS 1/10, Stryker Orthopaedics, Mahwah, New Jersey, Jan. 2010.
Silverton, Craig D. et al., Complications of a Cable Grip System, The Journal of Arthroplasty, Vo. 11, No. 4, Jun. 1996 pp. 400-404.
Smith & Nephew, Accord Cable System, Jan. 2004, 7138-0896, Smith & Nephew, Inc., Memphis, Tennessee, US.
Stryker, Dall-Miles Cable System: Beaded Cable & Single-Sided Tensioner, Literature No. LDMCSB; May 2004, Stryker Corporation, Mahwah, New Jersey, US.
SuperCable: Polymer Iso-Elastic Cerclage System, Kinamed Inc., 2015, B00110 G, ISO 13485, FM 75124, Camarillo, California, US.

* cited by examiner

TENSIONING CABLE LOCKING DEVICE

CROSS-REFERENCE TO RELATED APPLICATIONS

This application claims the benefit of the filing date of U.S. Provisional Patent Application No. 62/454,266 filed Feb. 3, 2017, the disclosure of which is hereby incorporated herein by reference.

TECHNICAL FIELD

The present invention generally relates to orthopedic surgery involving bone fixation systems for repairing fractured bones and, more particularly, cable loop systems comprising a tension device.

BACKGROUND OF THE INVENTION

Bone fixation systems are commonly used for repairing fractured bones. In some cases, the bone fragments are too small to use screws for proper fixation. In other cases, at least one of the bone fragments has an intramedullary implant within the bone that may prevent a screw (e.g., a bicortical screw) from being properly placed. As an alternative to using screws, many surgeons use cable loop systems to provide supplemental fixation.

Cable loop systems are known in the art. For example, U.S. Pat. Nos. 8,142,434 and 5,964,769, hereby incorporated by reference in their entirety, disclose cable loop systems for repairing fractured bones.

Such a system may comprise a connector for holding a cable in a loop around a bone, a cable tensioner for tensioning the cable around the bone, and a crimping tool for fixing the cable in place. The system may further comprise a cutting tool to cut the end of the cable after tensioning.

In some applications, existing cable loop systems are undesirable because installation requires special tools, such as cable tensioners, that are bulky, heavy, and hard to work with. Moreover, the cable may lose tension over time and there is no way to retighten the cable intraoperatively or postoperatively using these tools. For example, any amount of bone loss or shifting of bone fragments may cause the entire cable loop system to lose tension.

Also, there is also no way to use these tools to measure the amount of cable elongation during tensioning.

Additionally, when the end of the cable is cut after tensioning, frayed ends may be left exposed at the surgical site.

Thus, there remains a need for a cable loop system that is easy to install, using simplified tools.

BRIEF SUMMARY OF THE INVENTION

One aspect of the present invention provides a tension device for applying tension to a cable looped at least once around a bone. The tension device in accordance with this aspect of the invention preferably includes a body and a tension component for applying the tension force. The body may have first and second sections, and the body may have superior and inferior surfaces. The first section of the body may be adapted to secure a first end of the cable, and the second section of the body may be adapted to receive a second end of the cable. Desirably, the tension component is configured to remain implanted in vivo after the completion of the surgical procedure in which the tension device is used.

In accordance with some further aspects of the above tension device, the body may have an internal cavity. The tension component may be disposed within that internal cavity. In accordance with some yet further aspects of the tension device, the tension component may be a rotating spool that rotates in a first direction to tension the cable. According to some even further aspects, the cavity may include inward facing protrusions adapted to engage the tension component to prevent rotation of the spool in a second direction opposite the first direction. In accordance with some of such aspects, the spool may include a central cylinder with two outer flanges. The flanges may include outward facing protrusions to engage with the inward facing protrusions of the cavity.

In accordance with other aspects of the tension device, the spool may include a driver interface adapted to detachably receive a driver such that actuation of the driver in a first direction rotates the spool in the first direction. In accordance with yet other aspects of the tension device, the spool may include an inner ring and an outer ring with an elastic layer bonded therebetween. Desirably, the elastic layer in accordance with those aspects is adapted to bias the spool in the first direction. According to yet other aspects of the tension device, the spool may include a central cylinder and outer flanges. Desirably, the outer flanges are made of an elastic material so as to bias the spool in the first direction. Yet other aspects of the tension device may provide a cover plate disposed on the superior surface of the body of the tension device. According to some of those aspects, the cover plate may include a window and a reference marker. Additionally, the spool may include corresponding indicia for measuring cable elongation during tensioning.

In accordance with some other aspects of the tension device, the spool may have a tunnel spanning its diameter. Desirably, such tunnel may be adapted to receive the second end of the cable. In accordance with other aspects, a locking component may selectively secure a rotational position of the spool. In accordance with yet other aspects, a pin may be insertable through a bore at the center of the spool and at least partially into the body of the tension device. According to some of those aspects, a spring component may be positioned between the pin and the spool. Desirably, such spring component may be adapted to bias the spool in the first direction.

According to other aspects of the above tension device, the first section of the body may have an opening shaped to receive the cable therethrough while preventing a bead at the first end of the cable from passing through the opening. In some of such aspects, the opening may define an elastic rim that is adapted to apply tension on the cable. In some other of such aspects, the opening may include a compression spring therein to apply tension on the cable.

According to other aspects of the tension device, an interface between the first and second sections of the body may include at least one spring component. According to yet other aspects, the body may include a third section extending in a proximal or distal direction. Desirably, the third section includes a throughbore adapted to receive the second end of the cable when the cable is looped at least twice around the bone. In yet other aspects of the tension device, the inferior surface of the body of the tension device is arcuate shaped. In still other aspects of the tension device, the inferior surface of the body may include spikes adapted to contact bone. Still other aspects of the device may include a porous coating on the inferior surface of the body. Desirably, that porous coating is adapted to promote bone ingrowth.

According to some other aspects of the tension device, the tension device may include an indicator scale to measure and/or display the tension force carried by the cable. According to yet other aspects, a torque limiting component may be provided. Such torque limiting component may be connected between the driver interface and the cable. According to other aspects of the tension device, the tension component may include a cable clamp for securing the second end of the cable to the tension device.

Another aspect of the present invention provides a method of using a cable loop fixation system. The method in accordance with this aspect of the invention preferably includes: using a first tension device during a surgical procedure to tension a first cable looped at least once around a bone in a patient's body; and then leaving the first tension device in the patient's body after the surgical procedure. Desirably, the step of leaving the first tension device in the patient's body after the surgical procedure includes closing a surgical incision while the first tension device remains implanted in the patient's body.

In accordance with some further aspects of the above method, the step of using the first tension device to tension a first cable includes rotating a tension component in a first direction. In accordance with yet other aspects of the method, the step of leaving the first tension device in the patient's body includes exerting a spring force on the first cable by the first tension device. Desirably, the first tension device is configured such that at least some of the spring force is maintained indefinitely. In accordance with some other aspects of the method, the cable may be looped at least once around a bone plate that is in contact with the bone.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION

Those of skill in the art will recognize that the following description is merely illustrative of the principles of the invention, which may be applied in various ways to provide many different alternative embodiments.

Figure 1:
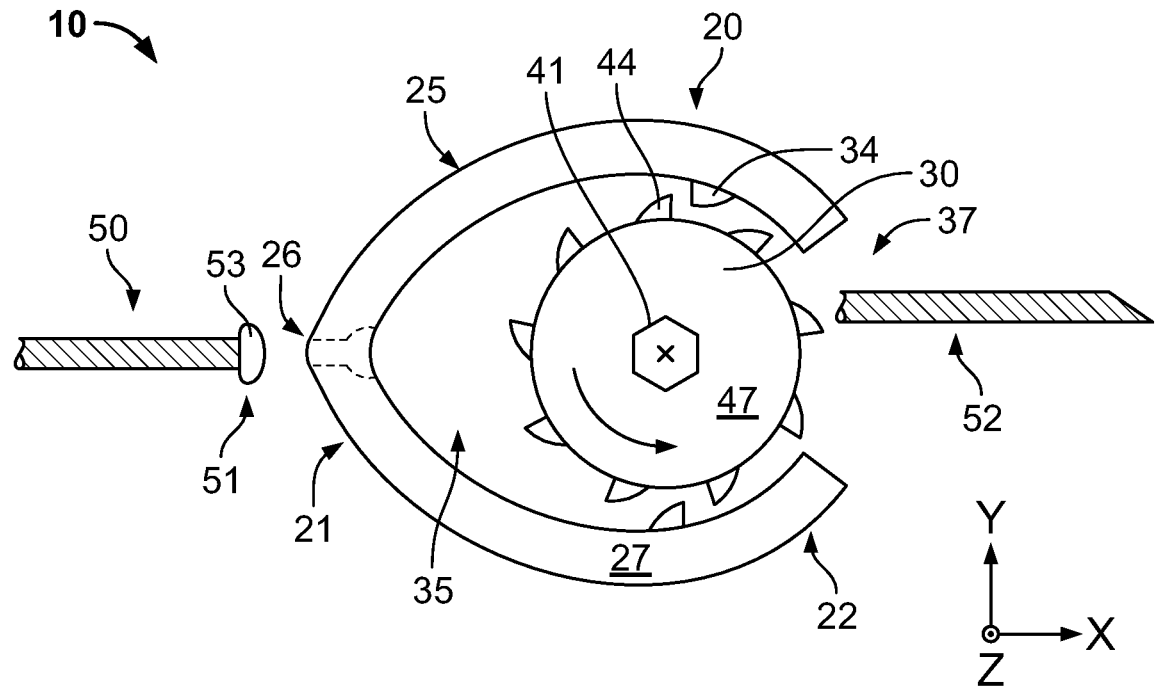
FIG. 1 shows a top view of a cable loop system according to one embodiment.

FIG. 1 shows a cable loop system 10 according to one embodiment of the present invention. System 10 comprises a tension device 20 and a cable 50.

Tension device 20 includes a body 25 having first and second sections 21, 22 and superior and inferior surfaces 27, 29. First section 21 is adapted to secure a first end 51 of cable 50, while second section 22 is adapted to receive a second end 52 of cable 50. Tension device 20 may be comprised of any suitable biocompatible material such as titanium or stainless steel.

Figure 2:
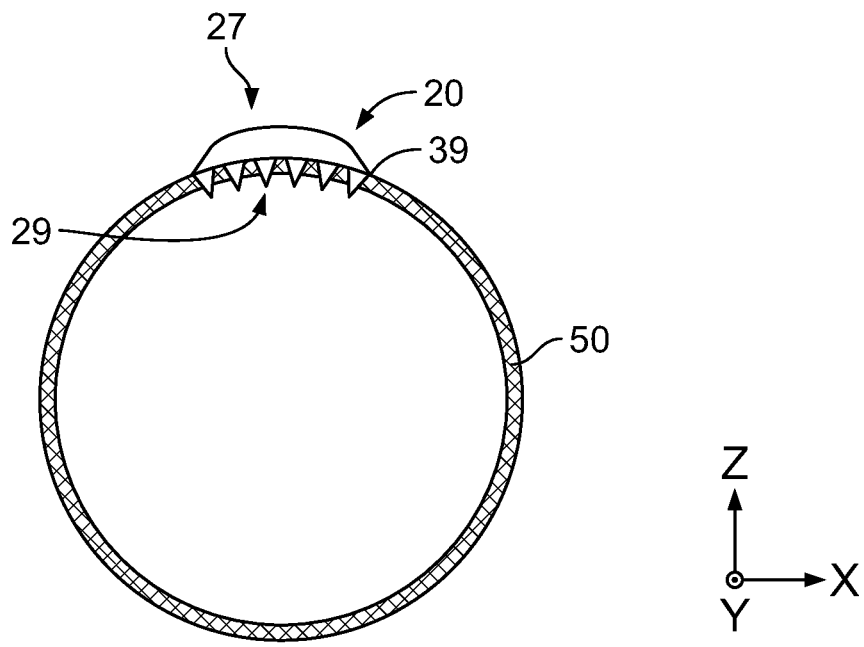
FIG. 2 shows a side view of the cable loop system of FIG. 1.

Inferior surface 29 may be arcuate and, in some embodiments, may be adapted to contact bone. Further, the inferior surface 29 may include spikes 39 adapted to grip the bone (FIG. 2). In other embodiments, the inferior surface 29 may include a porous coating between the bone and inferior surface 29 to promote bone ingrowth.

Figure 3:
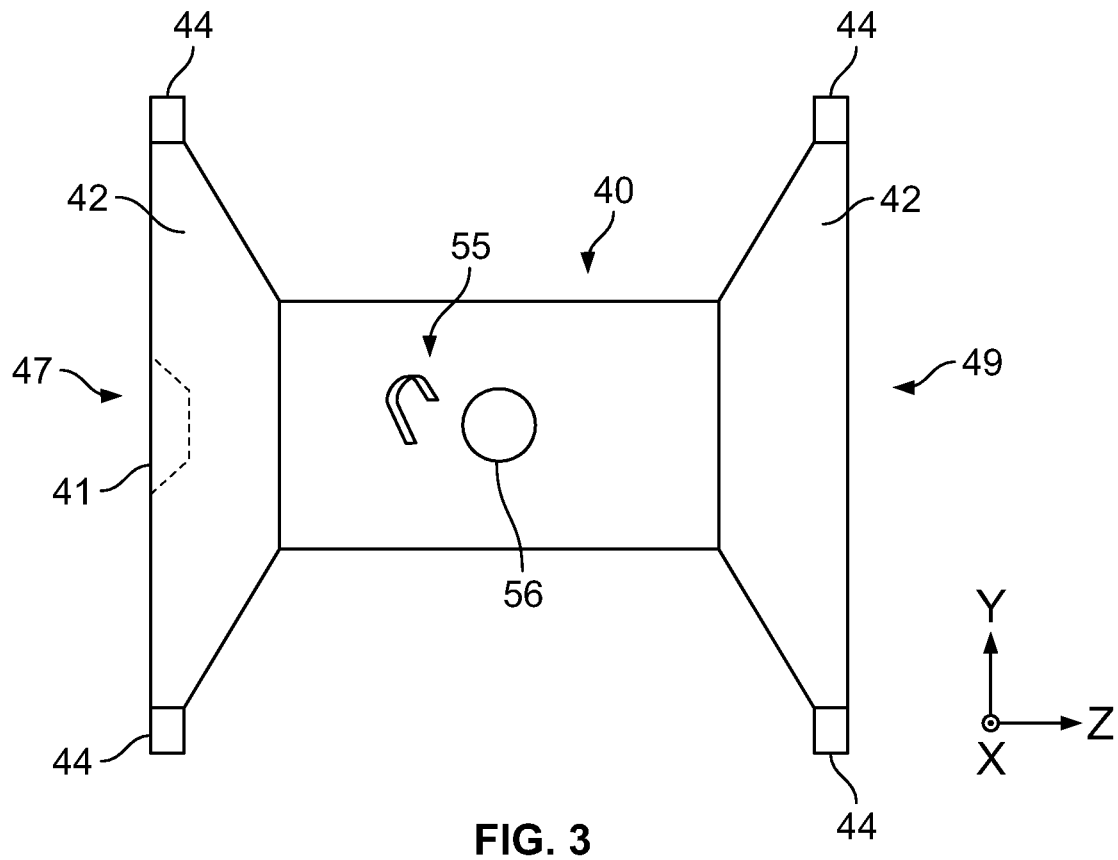
FIG. 3 shows a side view of a component of a tension device according to one embodiment.

Body 25 has an internal cavity 35 and an opening 26 in the first section 21 extending into cavity 35 (FIG. 3). The second end 52 of cable 50 is insertable through opening 26. Body 25 also has another opening 37 in the second section 22 extending into cavity 35. Both first and second ends 51, 52 of cable 50 are insertable through opening 37. Accordingly, in many embodiments, opening 37 may be larger than opening 26.

Alternative embodiments of body 25 may instead include an opening 66 in the first section 21 that does not extend into cavity 35. For example, the embodiment of FIG. 9 has opening 66 which communicates with a lateral slot 76 adapted to receive a bead 53 on the first end 51 of cable 50, as discussed below.

Referring to FIG. 3, cavity 35 has a tension component 30 disposed therein. Cavity 35 also may include inward facing protrusions 34 adapted to engage with the tension component 30.

In a preferred embodiment, the tension component 30 is a rotating spool. As shown in FIG. 3, spool 30 comprises a central cylinder 40 extending along an axis Z transverse a central longitudinal axis of the bone Y. The cylinder 40 has superior and inferior surfaces 47, 49, corresponding to the superior and inferior surfaces of body 25. Thus, spool 30 rotates about the Z axis.

Figure 4:
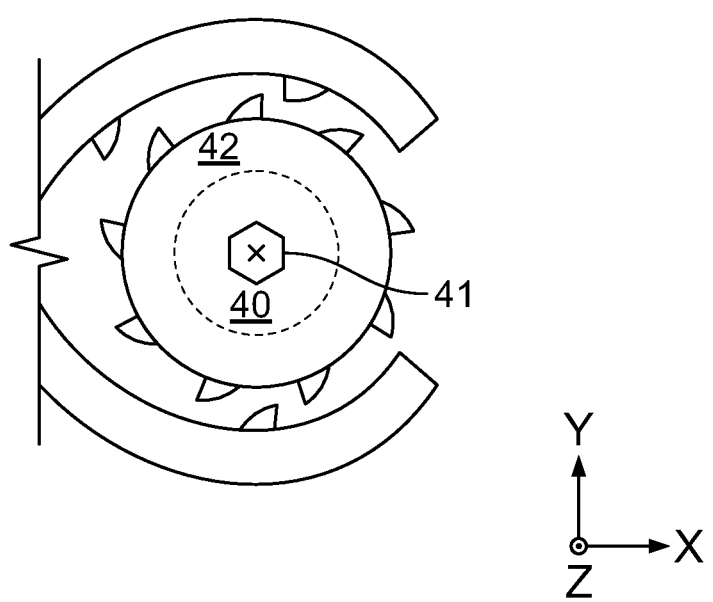
FIG. 4 shows a top view of the component of FIG. 3.

Moreover, as shown in FIG. 4, superior surface 47 of cylinder 40 may include an interface for engaging with a driving tool, such as a hex drive socket 41 adapted to receive a screwdriver. In that manner, actuation of the driving tool in a counterclockwise direction rotates the spool in the counter-clockwise direction. Desirably, the configuration of the driver interface may be a standardized one, such as that used on bone screws, so as to reduce the need for specialized tools in order to operate the device.

Additionally, cylinder 40 may also include a fastening component such as a cable clamp 55, as shown in FIG. 3, for securing the second end 52 of cable 50 to the cylinder 40. Accordingly, when spool 30 rotates, clamp 55 can help wrap and retain cable 50 around the Z axis of spool 30.

In some embodiments, cylinder 40 may additionally, or alternatively, include a throughbore 56 spanning its diameter along an axis X transverse the central longitudinal axis of the bone Y (FIG. 3). Throughbore 56 can be adapted to receive the second end 52 of cable 50. It is also possible for cylinder 40 to alternatively include a bore 58 (not shown) extending at least partially through cylinder 40 along the X axis and exiting the superior surface 47, for example, along the Z axis. Bore 58 may also be adapted to receive the second end 52 of cable 50. The cable 50 can thus be secured to the spool 30 by passing the second end 52 of the cable 50 through either throughbore 56 or bore 58 and then rotating the spool 30 to begin wrapping the cable 50 around the cylinder 40. It is noted that, although the cylinder 40 is shown as having a circular cross-section in the X-Y plane, the cylinder 40 may have any appropriate shape for allowing the cable 50 to be wrapped around it.

Moreover, in certain applications, it may be desirable for the spool 30 to provide a torque limiting or torque indicating function. For example, cylinder 40 may be subdivided into an inner member 40a and an outer member 40b concentrically arranged with respect to one another and at least somewhat rotatable independently of one another (not shown). In a torque limiting arrangement, a torque limiting component 110 may be disposed between the inner and outer members 40a, 40b. The inner member 40a may include the hex drive socket 41 and the outer member 50b may be adapted to receive the second end 52 of cable 50.

The torque limiting component 110 may have one or more engagement features 115 (not shown) disposed between the inner member 40a and the outer member 40b that are configured to disengage with each other when a predetermined amount of tension force is applied to cable 50, i.e. the tension limit. When the tension limit is reached, inner member 40a may continue to rotate, but outer member 40b may no longer rotate or apply additional tension force to cable 50.

In a torque indicating function, an elastic connection may be provided between the inner member 40a and the outer member 40b, so that the relative displacement between the inner member 40a and the outer member 40b indicates the amount of torque applied and/or the amount of tension in the cable 50. Indicia, such as graduated markings, may be provided on the inner and outer members 40a, 40b to help show the relative displacement between the inner and outer members 40a, 40b and/or to display the amount of torque/tension applied. Further, in certain applications, torque limiting and/or torque indicating components may be incorporated into the driving tool that is adapted to engage with hex drive socket 41.

In a preferred embodiment, spool 30 is free-floating within cavity 35. That is, spool 30 does not rotate about a central spindle or pin that is fixed to the body 25. Rather, the perimeter of the cavity 35 desirably constrains the position of the spool 30 within the body 25, such as by defining a generally or partially concentric space within which the spool 30 is rotatable.

In other embodiments, spool 30 may further comprise a pin 31 insertable through a central bore 33 (not shown) in cylinder 40 and at least partially into body 25. The pin 31 may be configured to lock the rotation of the spool 30. For example, bore 33 may extend along the Z axis and pin 31 may be movable within bore 33 between an unlocked and locked position in order to selectively lock spool 30 in place. In the unlocked position, spool 30 is free to rotate about pin 31. Alternatively, in the locked position, locking features on pin 31 will move into engagement with corresponding features on spool 30 such that spool 30 cannot unwind, or alternatively cannot rotate in either direction. For example, pin 31 may include tabs that fit into recesses on spool 30 in the locked position.

In addition, in some applications, it may be desirable to include a spring component 32 (not shown), such as a torsion spring, positioned between pin 31 and spool 30, wherein the spring component 32 is biased in the counter-clockwise direction. That biasing preferably helps maintain tensile force on the cable, which may help prevent loosening of the cable loop system, such as when there has been bone loss or shifting of bone fragments after the surgical procedure.

Figure 5:
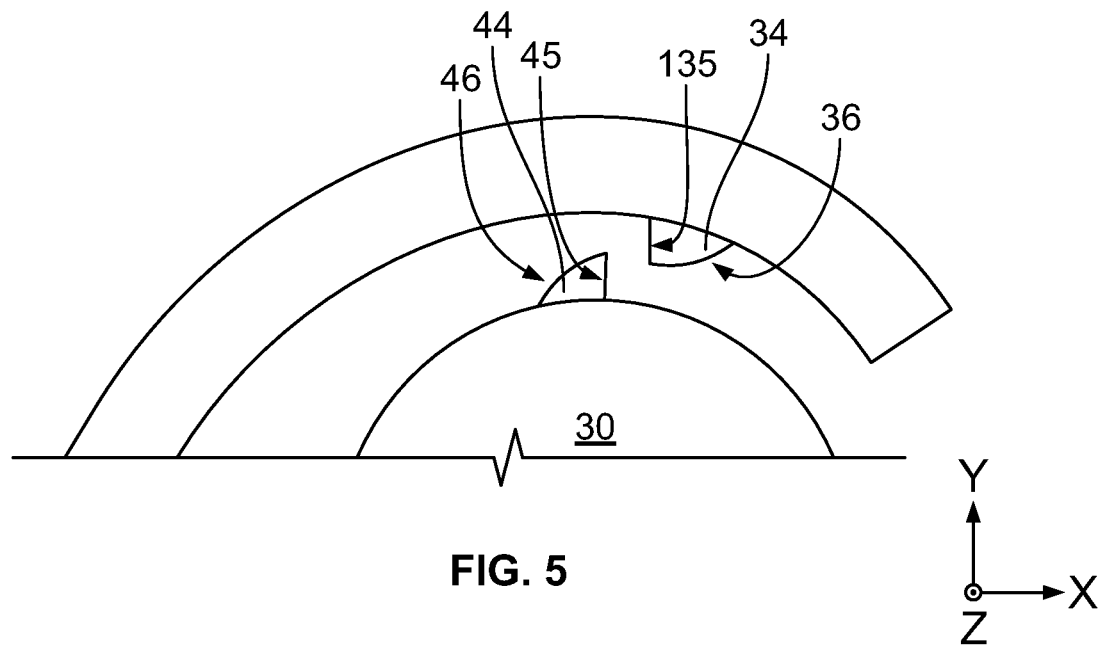
FIG. 5 shows an enlarged top view of certain features of the tension device of FIG. 3.

As shown in FIG. 3, spool 30 further comprises two outer flanges 42. In certain embodiments, outer flanges 42 may include outward facing protrusions 44 engageable with inward facing protrusions 34 of cavity 35. Protrusions 34, 44 are configured to engage one another like a ratchet, such that spool 30 can only rotate in one direction. More specifically, as shown in FIG. 5, protrusions 34 have a vertical wall 135 and a sloping wall 36, similar to protrusions 44 having a vertical wall 45 and a sloping wall 36. When spool 30 is rotated in the counter-clockwise direction, sloping wall 36 rides along sloping wall 46 such that spool 30 can rotate. In contrast, when spool 30 is rotated in the clockwise direction, vertical wall 135 abuts vertical wall 45 preventing rotation. By preventing rotation in the clockwise direction, vertical walls 135, 45 of protrusions 34, 44 can help maintain tension in the cable loop system.

In certain applications, the vertical walls 135 of the protrusions 44 may include a spring 43 (not shown) that is compressed against the vertical walls 45 of protrusions 34, or vice versa, when the cable 50 is tensioned. Compression of spring 43 preferably applies a biasing force that resists clockwise rotation of the spool 30 and maintains tension of the cable 50.

It is also possible for outer flanges 42 to be made of an elastic material, which may help maintain tensile force on the cable 50 and prevent loosening of the cable loop system 10. That is, when the cable 50 is tensioned, a reactive force may be applied to the outward facing protrusions 44 of the flanges 42 by the inward facing protrusions 34 of the cavity 35, causing the elastic material of flanges 42 to deform somewhat in the circumferential direction. Elastic deformation of flanges 42 preferably applies a biasing spring-like force that resists clockwise rotation of the spool 30 and maintains tension of the cable 50, thereby preventing loosening of the cable loop system 10.

Figure 10:
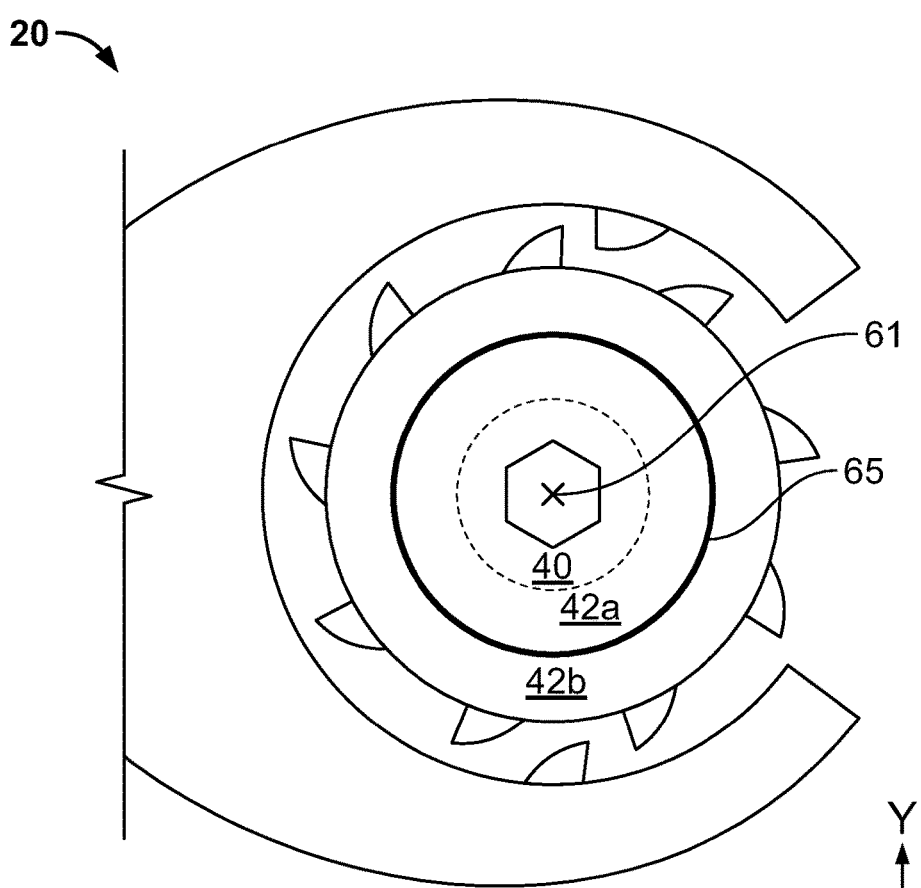
FIG. 10 shows a top view of a component of a tension device according to a further embodiment.

In some alternative embodiments, as shown in FIG. 10, flanges 42 of spool 30 may comprise an inner ring 42a and an outer ring 42b made of rigid materials with an elastic layer 65 bonded therebetween. Cylinder 40 may include an interface for engaging with a driving tool, such as a hex drive socket 61, as discussed above. Accordingly, when cable 50 is tensioned, a reactive force may be applied to the outward facing protrusions 44 of the flanges 42 by the inward facing protrusions 34 of the cavity 35, causing the elastic layer 65 to deform somewhat in the circumferential direction. Elastic deformation of layer 65 may apply a biasing spring-like force that maintains tension of the cable 50 in a similar manner to the elastic flanges 42 discussed above.

Figure 6:
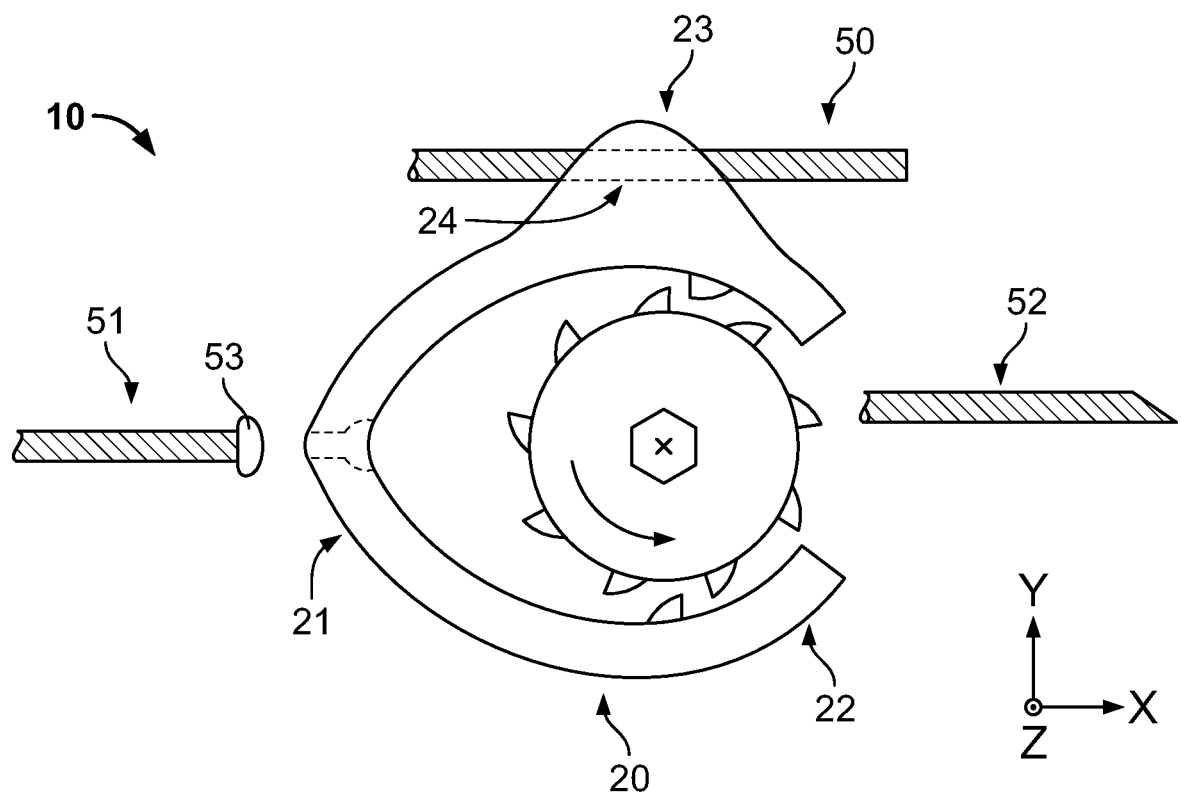
FIG. 6 shows a top view of a cable loop system according to a second embodiment.

Often, body 25 of tension device 20 may have a third section 23 extending in a distal or proximal direction along the central longitudinal axis Y. As shown in FIG. 6, third section 23 extends in a proximal direction and includes a throughbore 24 adapted to receive the second end 52 of cable 50. Including the third section 23 may be desirable in cases when cable 50 is looped around a bone more than once. For example, cable 50 may be looped around the bone twice to help evenly distribute the cable tension over a larger bone area. Thereafter, cable 50 may be passed through the throughbore 24 to help keep cable 50 in position.

Figure 7:
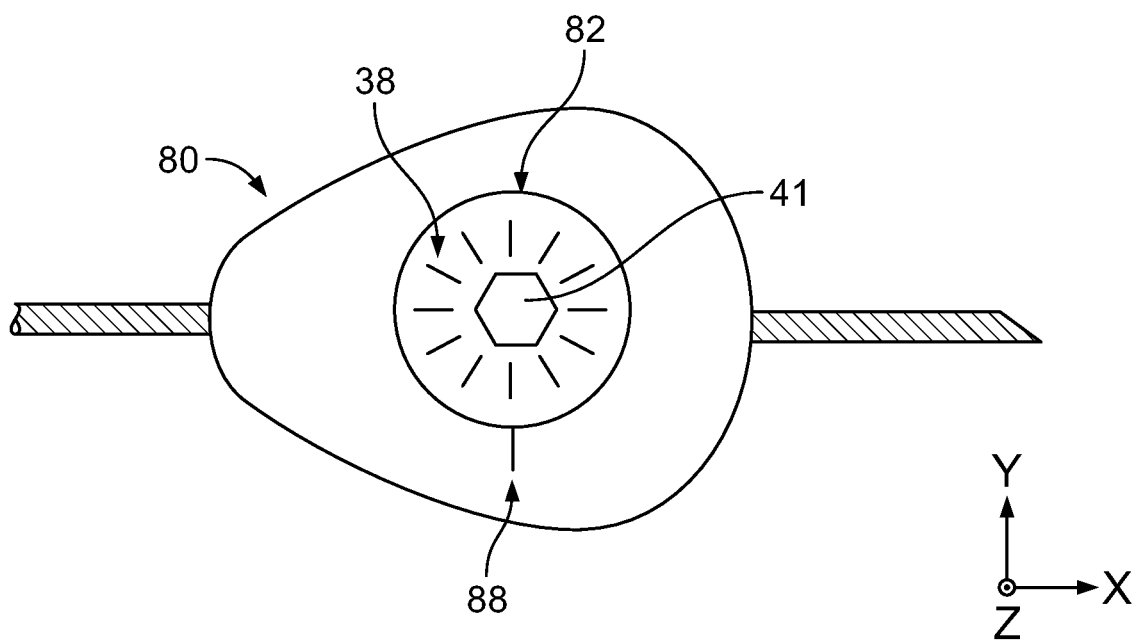
FIG. 7 shows a top view of a cover plate according to one embodiment.

Tension device 20 may additionally comprise a cover plate 80 disposed on the superior surface 27 of body 25. Cover plate 80 may prevent spool 30 escaping cavity 35 in a direction along the Z axis. As shown in FIG. 7, cover plate 80 can include a window 82 to provide access to the hex drive socket 41 disposed on spool 30. It is also possible to view indicia 38 on spool 30 through window 82.

Indicia 38 may align with a reference marker 88 on cover plate 80 in order to measure the amount of cable elongation during tensioning. For example, a surgeon can monitor the location of indicia 38 relative to the reference marker 88 to determine the number of spool rotations. Then, the surgeon can calculate the amount of excess cable retained on spool 30. These measurement tools 38, 88 may help the surgeon tension the cable 50 in a controlled manner and/or to a specified degree.

The cover plate 80 may further include a digital tension gauge 120 (not shown) to display the amount of tension force being applied to the cable 50. Alternatively, the tension gauge may be incorporated into the driving tool.

Referring now to cable 50, first end 51 includes bead 53 having a larger diameter than opening 26 in the first section 21 of the body 25 (FIG. 1). Thus, first end 51 cannot pass through opening 26. In contrast, second end 42 is a free end and can pass through opening 26.

Opening 26 may include a bore 103 (not shown) that includes a compression spring 105 (not shown) disposed therein. Bore 103 may have a diameter as large as or larger than the bead 53 at the first end of the cable 50 such that the bead 53 causes compression of spring 105 along the X axis when the cable 50 is tensioned. Thus, spring 105 preferably applies a force that maintains tension on the cable 50.

Figure 11:
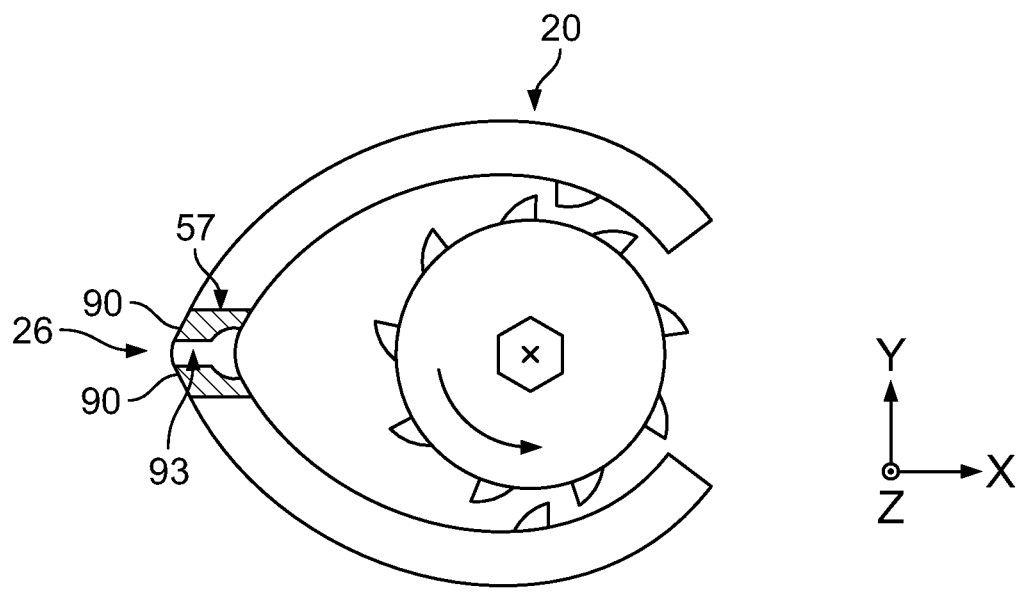
FIG. 11 shows a top view of a tension device according to a different embodiment.

In certain embodiments, opening 26 may define an elastic rim 57 that is structured to apply a biasing spring-like force on the first end 51 of cable 50, so as to maintain the tension of cable 50. For example, as shown in FIG. 11, the elastic rim 57 may be comprised of an annular elastic member 90 secured within a bore 93 having a diameter as large as or larger than the bead 53 at the first end of the cable 50. When cable 50 is tensioned, the elastic member 90 may deform somewhat along the X axis and apply a reactive force on bead 53. Thus, elastic rim 57 may provide a biasing spring-like force that maintains tension on the cable 50.

Figure 12:
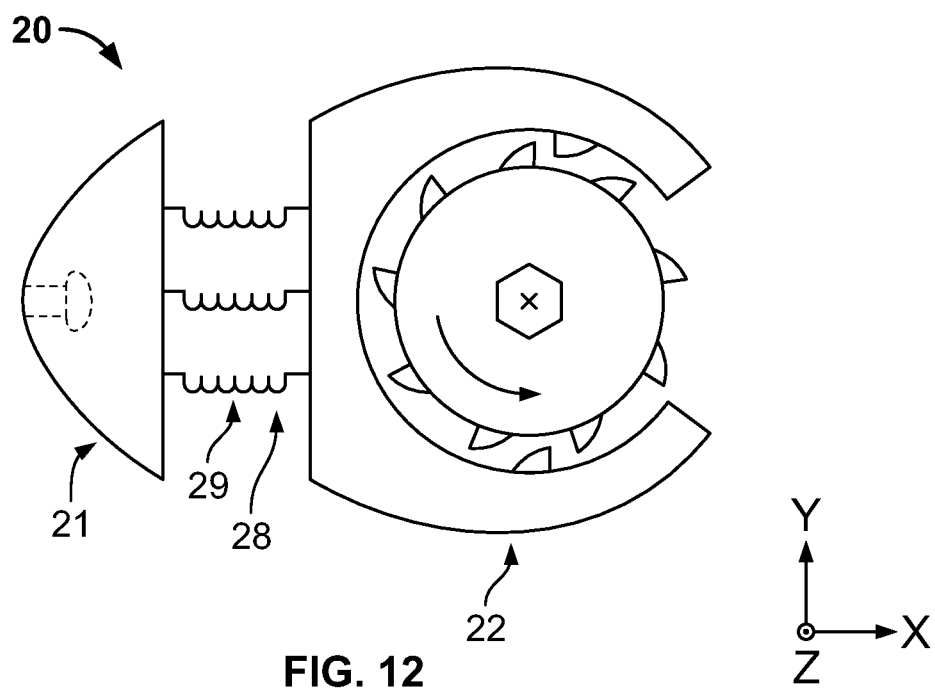
FIG. 12 shows a top view of a tension device according to an alternative embodiment.

Alternatively, as shown in FIG. 12, the first and second sections 21, 22 of the body may be movably connected together via an interface 28 that includes a spring-like component 29 that similarly maintains a tensioning force on the cable 50. Ultimately, a resistive force can help prevent loosening of the cable system 10.

Cable 50 may be made of any suitable biocompatible material including various polymers and metals. Cable 50 may also be made from strands of one or more materials. In the preferred embodiment, cable 50 is made from a nonmetallic, flexible material.

In operation, a surgeon may feed the second end 52 of cable 50 through opening 37 in the second section 22 of body 25, then through cavity 35, and finally through opening 26 in the first section 21 of body 25. The surgeon may continue to pass cable 50 through openings 26, 37 until the first end 51 of cable 50 reaches opening 26. More specifically, bead 53 may stop the first end 51 of cable 50 from passing through opening 26 such that the first end 51 of cable 50 is anchored in the first section 21 of body 25.

Figure 9:
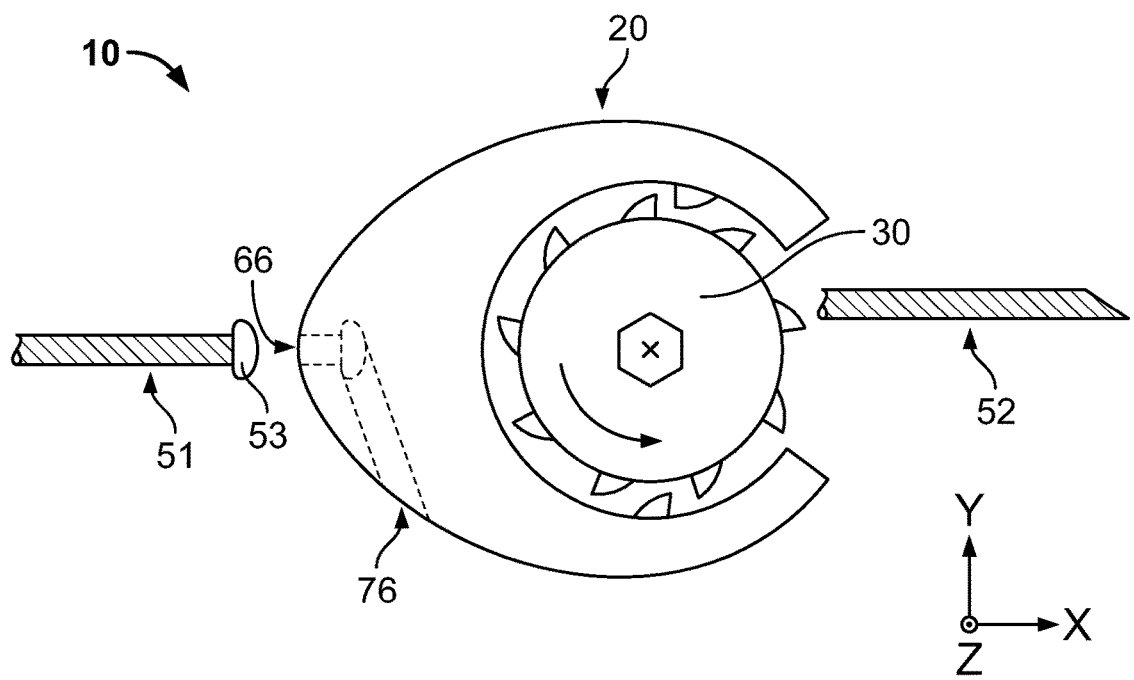
FIG. 9 shows a top view of a cable loop system according to yet another embodiment.

Alternatively, for the embodiment shown in FIG. 9, the bead 53 may be passed through lateral slot 76 and engaged with the opening 66 to anchor the first end 51 of cable 50 in the first section 21 of body 25.

In some embodiments, system 10 may be available preassembled with the first end 51 of cable 50 already anchored in the first section 21 of body 25. In those embodiments, the surgeon need not feed the entire cable 50 through openings 26, 37. This may be desirable to shorten the duration of the procedure.

Figure 8:
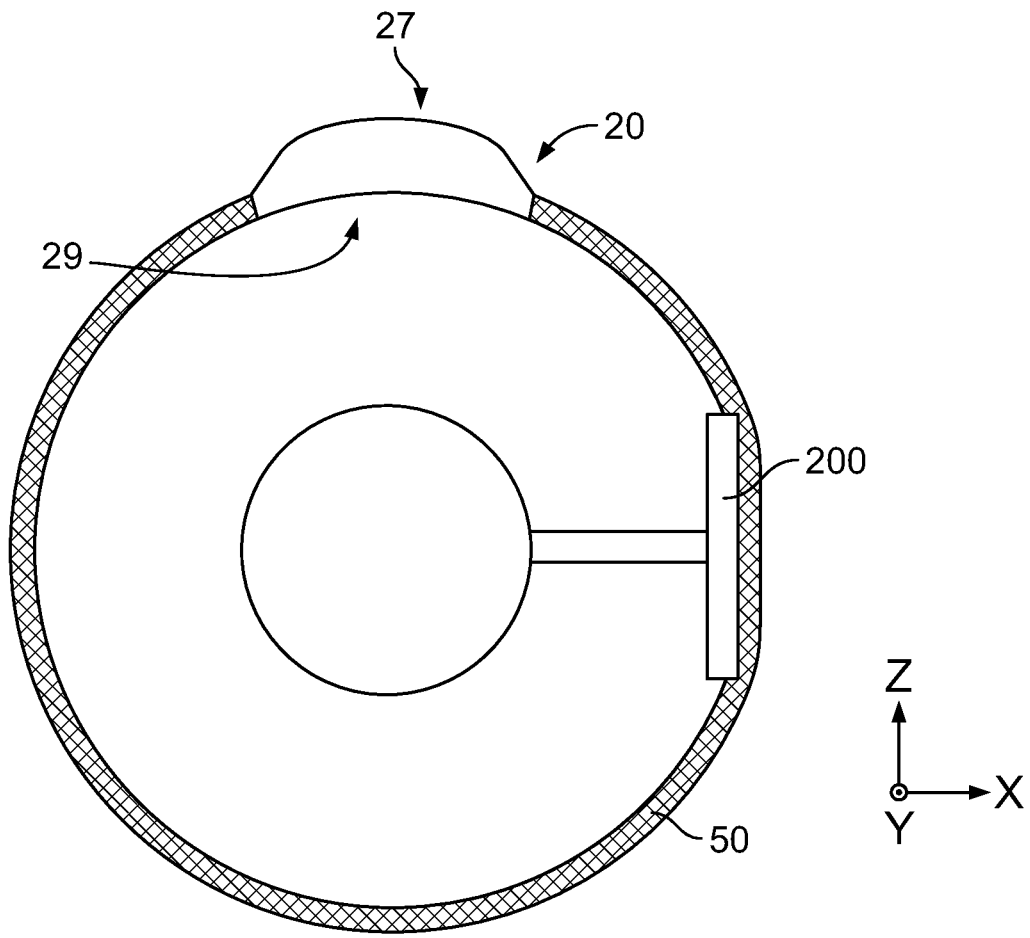
FIG. 8 shows a side view of a cable loop system according to another embodiment.

Once the first end 51 of cable 50 is secured, the surgeon may loop cable 50 at least once around the bone. In some cases, cable 50 may be looped more than once and cable 50 may be passed through a throughbore 24 in the third section 23 of the body 25. In some other cases, cable 50 may also be looped around a bone plate 200 in contact with the bone, as shown in FIG. 8. In yet other embodiments, the tension device 20 may be a part of or may be incorporated into the bone plate 200.

Often, tension device 20 may be available preassembled with the spool 30 disposed in cavity 35. Thus, the surgeon can feed the second end 52 of cable 50 into opening 37 and onto spool 30. At this point, it may be desirable to use a cable clamp 55 to secure the second end 52 of cable 50 in position. Alternatively, the surgeon may pass the second end 52 of cable 50 through a bore 56, 58 in spool 30 to secure cable 50 in position.

Next, the surgeon may use a screwdriver to actuate hex drive socket 41 and rotate spool 30 in a counterclockwise direction, thereby winding cable 50 around the Z axis of spool 30. Thus, the surgeon may tension cable 50 and monitor indicia 38, 88 to measure the amount of cable elongation during tensioning.

Once the surgeon has installed the first system 10, the surgeon may repeat the steps with a second cable loop system 100 in a distal or proximal direction along the Y axis. While the surgeon is installing the second system 100, the surgeon can monitor the tension in cable 50 in the first system 10.

During surgery, the surgeon can optionally loosen and/or tighten the cables in the first and second cable loop systems 10, 100 as desired. As such, tension device 20 can be reused in multiple applications.

In the preferred embodiment, spool 30 is free floating and has projections 44 that engage with projections 34 so, to loosen cable 50, the surgeon may remove the spool 30 from cavity 35 and manually rotate the spool 30 in a clockwise direction. The first section 21 of the body 25 may also include a quick release feature to disengage bead 53 from opening 26, 66 such that the surgeon can freely manipulate the first end 51 of the cable 50, for example in order to reposition and/or disengage the system. The first section 21 of the body 25 may alternatively include multiple positions for the bead 53 to be secured along the X axis, so that the cable 50 can be loosened (e.g., for repositioning the system) by popping the bead 53 into another position further away from the second section 22.

In another embodiment, spool 30 is not free floating and, instead, spool 30 is rotatable about a pin 31. In such an embodiment, the pin 31 may have unlocked and locked configurations, as discussed above, and the device may not have interacting projections 34, 44. Thus, in such an embodiment, in order to loosen cable 50, the surgeon may move pin 31 into an unlocked position and allow the spool 30 to rotate in a clockwise direction.

Once the cable 50 is tensioned to the preferred degree, the surgeon may position cover plate 80 over the tension device 20 to contain spool 30 within cavity 35. In certain embodiments, the surgeon may move the pin 31 to the locked position before positioning the cover plate 80.

Ultimately, tension device 20 is configured to remain in situ so there is no need for removal. In some embodiments, protrusions 34, 44 may resist clockwise rotation and maintain tension of the cable 50 to prevent loosening of the cable loop system 10 over time. Moreover, biasing spring-like forces applied by the device 20, as discussed above, may also maintain tension on the cable 50.

Even so, if the system 10 did become loose, the cable loop system 10 is structured so that the surgeon could access the tension device 20 again and retighten cable 50.

In sum, cable loop system 10 can provide various desirable advantages compared to existing cable loop systems. For example, tension device 20 may be a small, multifunctional device that can eliminate the need for cumbersome tools, such as separate cable tensioners. Notably, there may be no need for a cutting tool when using tension device 20 because the excess cable 50 is wound and retained on spool 30. Thus, there may be no frayed ends exposed at the surgical site.

Additionally, the method of using tension device 20 can be relatively simple and inexpensive. In many cases, a surgeon may desire the ability to gradually apply tension in a controlled manner by using tension device 20. A surgeon may also appreciate the ability to monitor indicia to measure the amount of cable elongation during tensioning.

Although some of the embodiments described herein have suggested counterclockwise rotation of spool 30 causes tensioning of cable 50, those of skill in the art will recognize that the directions could be reversed such that clockwise rotation of spool 30 causes tensioning of cable 50. Similarly, although the first section 21 of body 25 may be adapted to secure the first end 51 of cable 50 and the second section 22 of body 25 may be adapted to receive the second end 52 of cable 50, the configuration could be reversed vice versa.

Moreover, although many of the embodiments described herein describe a cable 50, a suture or band made of suitable biocompatible material could be used with tension device 20 to provide proper bone fixation.

Although the disclosure herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A tension device for applying a tension force to a cable looped at least once around a bone, comprising:
   a body having first and second sections, superior and inferior surfaces, and an internal cavity, the first section adapted to secure a first end of the cable and the second section adapted to receive a second end of the cable such that a closed loop is defined by a combination of the body and a portion of the cable extending between the first section and the second section; and
   a tension component to apply the tension force to the cable, wherein the tension component is disposed within the cavity and configured to remain implanted in vivo after a surgical procedure in which the tension device is used, the tension component comprising a rotating spool having a central cylinder and outer flanges made of an elastic material, the rotating spool configured to rotate in a first direction to tension the cable;
   wherein the outer flanges made of the elastic material are a biasing component adapted to bias the spool or the cable so as to prevent loosening of the tension device.

2. The tension device of claim 1, wherein the cavity includes inward facing protrusions adapted to engage with the tension component and prevent rotation in a second direction opposite the first direction.

3. The tension device of claim 2, wherein the outer flanges include outward facing protrusions that engage with the inward facing protrusions of the cavity.

4. The tension device of claim 1, wherein the spool includes a driver interface adapted to detachably receive a driver such that actuation of the driver in the first direction rotates the spool in the first direction.

5. The tension device of claim 1 further comprising a cover plate disposed on the superior surface of the body.

6. The tension device of claim 5, wherein the cover plate includes a window and a reference marker, and wherein the spool includes corresponding indicia for measuring cable elongation during tensioning.

7. The tension device of claim 1, wherein the spool has a tunnel spanning its diameter, and wherein the tunnel is adapted to receive the second end of the cable.

8. The tension device of claim 1, wherein the spool includes a cable clamp for securing the second end of the cable to the spool.

9. The tension device of claim 1, wherein the first section of the body has an opening shaped to receive the cable therethrough while preventing a bead at the first end of the cable from passing through the opening.

10. The tension device of claim 9, wherein the opening defines an elastic rim.

11. The tension device of claim 1, wherein an interface between the first and second sections of the body includes at least one spring component.

12. The tension device of claim 1, wherein the body includes a third section extending in a proximal or distal direction, the third section including a throughbore adapted to receive the second end of the cable when the cable is looped at least twice around the bone.

13. The tension device of claim 1, wherein the inferior surface of the body is arcuate shaped.

14. The tension device of claim 1, wherein the inferior surface of the body includes spikes adapted to contact bone.

15. The tension device of claim 1, wherein the inferior surface of the body includes a porous coating adapted to promote bone ingrowth.

16. A cable loop system, comprising:
    the tension device of claim 1, and
    the cable adapted to be secured by the first section of the body of the tension device and adapted to be received by the second section of the body, wherein the cable is a non-metallic, flexible cable.

17. A tension device for applying a tension force to a cable looped at least once around a bone, comprising:
    a body having first and second sections, superior and inferior surfaces, and an internal cavity, the first section adapted to secure a first end of the cable and the second section adapted to receive a second end of the cable such that a closed loop is defined by a combination of the body and a portion of the cable extending between the first section and the second section; and
    a tension component to apply the tension force to the cable, wherein the tension component is disposed within the cavity and configured to remain implanted in vivo after a surgical procedure in which the tension device is used, the tension component comprising a rotating spool having an inner ring, and outer ring, and an elastic layer bonded therebetween, the rotating spool configured to rotate in a first direction to tension the cable; and wherein the elastic layer is a biasing component adapted to bias the spool or the cable so as to prevent loosening of the tension device.

18. A tension device for applying a tension force to a cable looped at least once around a bone, comprising:
- a body having first and second sections, superior and inferior surfaces, and an internal cavity, the first section adapted to secure a first end of the cable and the second section adapted to receive a second end of the cable such that a closed loop is defined by a combination of the body and a portion of the cable extending between the first section and the second section;
- a tension component to apply the tension force to the cable, wherein the tension component is disposed within the cavity and configured to remain implanted in vivo after a surgical procedure in which the tension device is used, the tension component comprising a rotating spool that rotates in a first direction to tension the cable;
- a biasing component adapted to bias the spool or the cable so as to prevent loosening of the tension device; and
- a cover plate disposed on the superior surface of the body, wherein the cover plate includes a window and a reference marker, and wherein the spool includes corresponding indicia for measuring cable elongation during tensioning.

* * * * *